(12) United States Patent
Park et al.

(10) Patent No.: US 6,794,605 B2
(45) Date of Patent: Sep. 21, 2004

(54) METHOD FOR FABRICATING CHEMICAL MECHANICAL POLSHING PAD USING LASER

(75) Inventors: Inha Park, Ulsan (KR); Tae-Kyoung Kwon, Ulsan (KR); Jaeseok Kim, Ulsan (KR); In-Ju Hwang, Ulsan (KR)

(73) Assignee: SKC Co., LTD, Kyunggi-do (KR)

( * ) Notice: Subject to any disclaimer, the term of this patent is extended or adjusted under 35 U.S.C. 154(b) by 47 days.

(21) Appl. No.: 10/110,800
(22) PCT Filed: Aug. 29, 2001
(86) PCT No.: PCT/KR01/01462
§ 371 (c)(1), (2), (4) Date: Dec. 2, 2002
(87) PCT Pub. No.: WO03/011520
PCT Pub. Date: Feb. 13, 2003

(65) Prior Publication Data
US 2003/0132207 A1 Jul. 17, 2003

(51) Int. Cl.[7] ............................................. B23K 26/38
(52) U.S. Cl. ........................ 219/121.69; 219/121.71; 219/121.72
(58) Field of Search .................. 219/121.6, 121.67, 219/121.68, 121.69, 121.71, 121.72, 121.85

(56) References Cited
U.S. PATENT DOCUMENTS 5,458,827 A * 10/1995 Holly .......................... 264/400
6,531,226 B1 * 3/2003 Petkie ......................... 428/408

FOREIGN PATENT DOCUMENTS

JP    2000-218512    * 8/2000

* cited by examiner

Primary Examiner—Samuel M. Heinrich
(74) Attorney, Agent, or Firm—Abelman, Frayne & Schwab

(57) ABSTRACT

Disclosed is a method for forming micro-holes, perforated holes, or grooves on a chemical mechanical polishing pad by a laser. This method involves the steps of determining a pattern of micro-holes, grooves, or perforated holes to be formed on a polishing pad, inputting the determined pattern to a computer numerical control (CNC) controller, and driving a laser device adapted to irradiate a laser beam and a table adapted to conduct a three-dimensional movement and rotation while supporting the polishing pad, under the control of the CNC controller based on the inputted pattern, thereby irradiating the laser beam from the laser device onto the polishing pad supported by the table while moving the table in accordance with the inputted pattern, so that micro-holes, grooves, or perforated holes having a pattern corresponding to the determined pattern are formed on the polishing pad. In accordance with the present invention, it is possible to form diverse patterns of micro-holes, perforated holes or grooves exhibiting superior effects in a polishing process.

5 Claims, 10 Drawing Sheets

METHOD FOR FABRICATING CHEMICAL MECHANICAL POLSHING PAD USING LASER

TECHNICAL FIELD

The present invention relates to a polishing pad used in a chemical mechanical polishing process, and more particularly to a method for forming micro-holes, perforations, or grooves on a polishing pad by a laser.

BACKGROUND ART

Generally, chemical mechanical polishing (CMP) is a high precision/mirrored surface polishing method used to obtain global planarization in a semiconductor device manufacturing process. In accordance with such CMP, a slurry is supplied between a polishing pad and a wafer to be polished, so as to chemically etch the surface of the wafer. Using the polishing pad, the etched surface of the wafer is mechanically polished.

Referring to FIG. 1, a typical CMP machine, which is denoted by the reference numeral 1, is schematically illustrated. Also, a CMP method using the CMP machine 1 is schematically illustrated in FIG. 2. The CMP method includes a chemical etching reaction process and a mechanical polishing process, which are conducted using a polishing pad 10 included in the CMP machine 1. The chemical etching reaction is carried out by a slurry 42. That is, the slurry 42 serves to chemically react with the surface of a wafer 30 to be polished, thereby making it possible for the mechanical polishing process, following the chemical etching reaction, to be easily carried out. In the mechanical polishing process, the polishing pad 10, which is fixedly mounted on a platen 20, rotates. The wafer 30, which is firmly held by a retainer ring 32, rotates while oscillating. A Slurry containing abrasive particles is supplied to the polishing pad 10 by a slurry supply means 40. The supplied slurry is introduced between the polishing pad 10 and the wafer 30. The introduced abrasive particles come into frictional contact with the wafer 30 by virtue of a relative rotating speed difference between the polishing pad 10 and the wafer 30, so that they conduct mechanical polishing. The slurry 42 is a colloidal liquid containing abrasive particles having a grain size of nanometers. This slurry 42 is spread on the polishing pad 10 during the polishing process. As the polishing pad 10 rotates during the polishing process, the slurry 42 supplied to the polishing pad 10 is outwardly discharged from the periphery of the polishing pad 10 due to a centrifugal force caused by the rotation of the polishing pad 10. In order to achieve an enhanced polishing efficiency, many abrasive particles should remain for a desirable lengthy period of time on the upper surface of the polishing pad 10 so that they participate in the polishing of the wafer. That is, the polishing pad 10 should make the slurry 42 be held on the surface thereof for as long a period of time as possible.

In order to make the slurry be held on the polishing pad for a long period of time, there may be used a method of forming spherical microcells having a size of micrometers (Em) or a method of forming perforations or grooves at the surface of the polishing pad. Such microcells, perforations and grooves act to control the flow and distribution of the slurry continuously supplied during the polishing process.

Conventionally, the formation of microcells at the polishing pad is achieved using a physical method or a chemical method. As the physical method, there is a method in which hollow microelements each having a cavity are incorporated in a polymeric matrix to form microcells. As the chemical method, there is a foaming method in which bubbles are chemically formed to form microcells.

The incorporation of microelements in a polymeric matrix is achieved by impregnating a large amount of microelements each having a cavity into a polymeric matrix in such a fashion that the microelements are uniformly distributed in the polymeric matrix, thereby forming microcells. The polymeric matrix is prepared by mixing a curing agent with a resin such as urethane, polyester, fluorinated hydrocarbon, or a mixture thereof. For the microelements, inorganic salt, sugar, water soluble gum, or resin is mainly used. Such microelements are made of polyvinylalcohol, pectin, polyvinyl pyrrolidone, polyethylene glycol, polyurethane or a combination thereof. Such microelements have an average diameter of about 150 Em. The microelements are uniformly distributed over the polymeric matrix in accordance with a high shear mixing process, so that they form uniform microcells. Referring to FIG. 3, microcells formed using the cavity bodies are illustrated. The pad formed with microcells in the above mentioned manner is subsequently cut into pieces each having a desired thickness to obtain a polishing pad. In each cut piece, microcells randomly distributed in the pad are opened at the cut surfaces of the cut piece, so that they are exposed in the form of a circular or oval cross section at the cut surfaces of the cut piece. The sizes and positions of the micro-cell cross sections exposed at the polishing surface of each polishing pad are random. Such random size and position of the exposed microcell cross sections serves to degrade a desired uniformity among polishing pads.

In accordance with the chemical method in which cells are formed using a foaming process, a polymeric matrix is formed by mixing a curing agent with a liquid-phase polyurethane forming substance having a low boiling point. Water or liquefied gas, which directly takes part in a chemical reaction to generate gas, is also used as a foaming agent, thereby producing bubbles to form cells in the polymeric matrix. The production of bubbles is achieved by way of a nucleation caused by a high shear mixing operation. A surfactant, which serves to achieve a reduction in surface tension, is also used to adjust the size of microcells, thereby achieving a desired uniformity of micro-cells. Microcells formed using the foaming process are shown in FIG. 4. Where cells are formed in accordance with the foaming process, however, there are problems in that the cells are too large to be applied to a CMP pad, that those cells have a non-uniform distribution, and that there is no method capable of adjusting the size and distribution of the cells.

The microcells formed using microelements each having a cavity or a foaming process have a spherical structure having a circular or oval cross-sectional shape. Due to such a shape, the microcells have a cross section varying in the thickness direction of the polishing pad. For this reason, the cross section of each microcell exposed at the polishing surface of the polishing pad is varied as the polishing pad is abraded during a polishing process. In other words, circular or oval microcells exposed at the polishing surface of the polishing pad are gradually reduced in diameter as the polishing process proceeds, and finally disappear. Eventually, microcells existing below the surface of the polishing pad without being exposed, are newly exposed at the polishing surface of the polishing pad.

Thus, the cross section of each microcell exposed at the polishing surface of the polishing pad is varied as the polishing pad varies in thickness during the polishing process. For this reason, there is a problem in that the polishing rate is non-uniform.

In order to form perforations or grooves at the polishing surface of the polishing pad, a mechanical machining method has been used which uses a cutting or milling process.

Referring to FIG. 5a, a cutter 70 for forming grooves is illustrated. When a polishing pad is machined using the cutter 70 mounted to a tool die on a lathe under the condition in which the polishing pad is rotated, grooves are formed on the upper surface of the polishing pad in the form of concentric circles, as shown in FIG. 5b. FIG. 5c is a cross-sectional view taken along the line A—A of FIG. 6b. Referring to FIG. 6b, an exemplary form of grooves formed using the cutter is illustrated. In FIG. 6b, the grooves are denoted by the reference numeral 75. An example of grooves having the form of concentric circles is disclosed in U.S. Pat. No. 5,984,769.

Referring to FIG. 6a, a horizontal milling machine 81 is shown, on which cutting saws 82 and spacers 83 are mounted. The cutting saws 82 are configured to move in an X-axis direction. A polishing pad 10 to be machined is moved in a Y-axis direction. In accordance with these movements, grooves 85 extending in a first direction are formed on the upper surface of the polishing pad 10. After the formation of the grooves 85, the polishing pad 10 is rotated 90°. In this state, grooves extending in a second direction orthogonal to the first direction are formed as the polishing pad 10 is moved in the Y-axis direction. Thus, grooves arranged in the form of a lattice are formed on the polishing surface, as shown in FIGS. 6b and 6c.

Referring to FIG. 7a, perforating pins are illustrated which serve to form perforations at a polishing pad. When a perforating operation is carried out using the perforating pins under the condition in which the polishing pad is moved in a Y-axis direction, perforations are formed on the polishing surface of the polishing pad, as shown in FIG. 7b. An example of such perforations is disclosed in U.S. Pat. No. 5,853,317.

Since the conventional methods, which are used to form grooves or perforations at a polishing pad, utilize a cutting process conducted by a lathe or milling, the grooves have a fixed pattern such as concentric circles or a lattice. For this reason, it is difficult to form a groove pattern capable of effectively controlling the flow of a slurry. In accordance with the method for forming perforations using perforating pins, the perforations have a fixed shape. Also, the perforations are formed as the perforating pins are simply moved in an X or Y-axis direction. For this reason, the perforations have a simple and fixed pattern. Thus, it is difficult to obtain an effective hole pattern desired in a CMP process.

In a polishing pad machined to have grooves or perforations using mechanical means, debris formed during the machining process may be left in the grooves or perforations. Such debris may form scratches on a surface being polished during the CMP process.

DISCLOSURE OF THE INVENTION

Therefore, the present invention has been made in order to solve the problems involved with microcells formed using microelements each having a cavity or a foaming process and grooves or perforations formed using mechanical means. The present invention proposes a method capable of easily forming micro-holes, grooves or perforations having effective and diverse patterns on a polishing pad.

An object of the invention is to provide a method for forming micro-holes having the same function as microcells while having a controlled uniform distribution and a controlled uniform size, in order to eliminate the disadvantages involved with conventional methods using microelements each having a cavity or a foaming process, that is, a non-uniformity in the size and distribution of microcells resulting in a reduction or non-uniformity in the polishing rate of a polishing process.

Another object of the invention is to provide a method for forming grooves or perforations having diverse shapes, sizes, and patterns to effectively control the flow of a slurry during a polishing process, in order to eliminate the disadvantages involved with conventional mechanical methods, that is, insufficient control for the flow of the slurry due to a fixed shape or pattern of grooves or perforations.

In order to accomplish these objects, the present invention provides a method for forming, on a polishing pad, microholes, grooves or perforations having diverse patterns desired by the user, in accordance with a laser machining principle.

In accordance with an embodiment of the present invention, there is provided a method for fabricating a chemical mechanical polishing pad comprising the steps of: determining a pattern of micro-holes, grooves, or perforated holes to be formed on a polishing pad; inputting the determined pattern to a computer numerical control (CNC) controller; and driving a laser device adapted to irradiate a laser beam and a table adapted to conduct a three-dimensional movement and rotation while supporting the polishing pad, under a control of the CNC controller based on the inputted pattern, thereby irradiating the laser beam from the laser device onto the polishing pad supported by the table while moving the table in accordance with the inputted pattern, so that micro-holes, grooves, or perforated holes having a pattern corresponding to the determined pattern are formed on the polishing pad.

BEST MODE FOR CARRYING OUT THE INVENTION

Now, the present invention will be described in detail in terms of its constitution and function, with reference to the annexed drawings.

The present invention utilizes a laser machining principle in the formation of micro-holes, grooves or perforations on a polishing pad. The laser machining method has a feature of reducing the area of a layer subjected to a thermal deformation. Also, the laser machining method is performed in a non-contact fashion, so that there is no abrasion of the tool. The laser machining method is also capable of precisely machining an article having a complex shape, eliminating generation of noise and vibrations, and maintaining a clean working environment. When a laser beam is irradiated onto the polishing surface of a polishing pad, it abruptly increases the surface temperature of the polishing pad. As a result, the material of the polishing pad is melted and evaporated at the surface region where the laser beam is irradiated onto the polishing pad. As the material of the polishing pad is removed in the above fashion at the laser-irradiated region, machining of a micro-hole, groove or perforation is completed.

Figure 8:
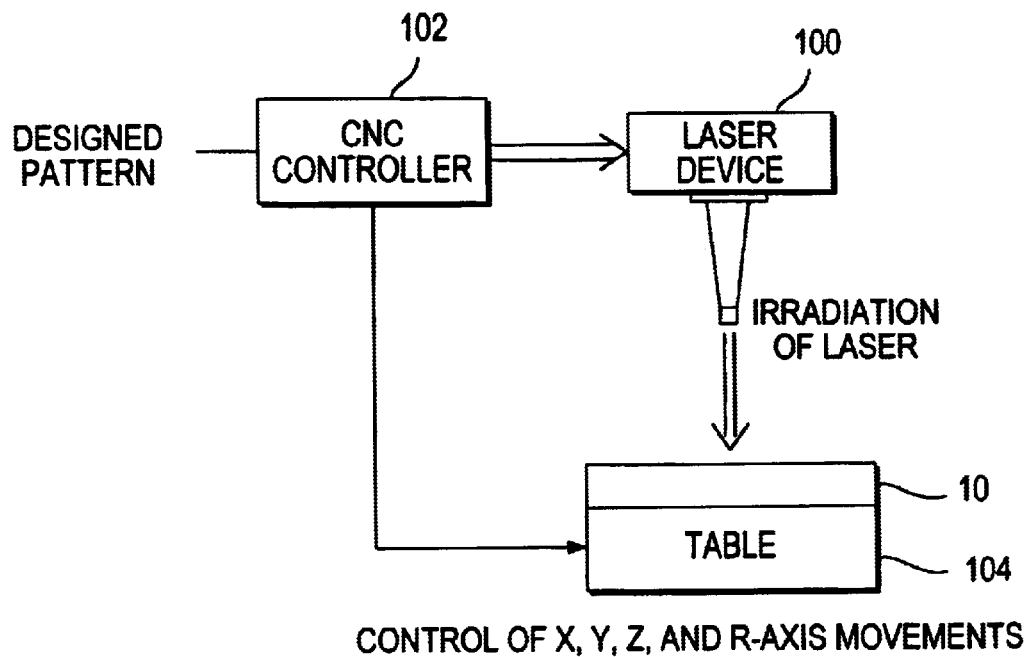
FIG. 8 is a schematic view illustrating a laser system used in the machining method according to the present invention.

Referring to FIG. 8, a laser machining system is illustrated which is used to carry out a laser machining method according to the present invention. As shown in FIG. 8, the laser machining system includes a laser device 100 for irradiating a laser beam, a table 104 for conducting a rotating movement and a three-dimensional movement, and a computer numerical control (CNC) controller 102 for controlling the laser device 100 and the table 104. A polishing pad 10 to be polished is mounted on the table 104.

The operator can freely determine the pattern of micro-holes, grooves, or perforations to be formed on a polishing pad, that is, the size, depth, and space of those micro-holes, grooves, or perforations.

The following description will be made only in conjunction with the formation of micro-holes. Of course, the formation of grooves or perforations is carried out in a manner similar to that of micro-holes.

The operator can select a desired shape of micro-holes from diverse shapes such as a circular shape, an oval shape, a triangular shape, and a rectangular or square shape. Also, the operator can freely determine the diameter, width, or depth of the micro-holes. The inclination of the micro-holes with respect to the polishing surface and the arrangement of the micro-holes can also be determined by the operator.

The pattern of micro-holes determined by the operator is inputted to the CNC controller 102. The pattern inputting may be achieved using a scanning method, a CAD, or other means. The CNC controller 102 recognizes the inputted pattern, and controls the laser device 100 and the table 104.

As the laser device 100 and table 104 are driven under the control of the CNC controller 102, a laser beam is irradiated onto the polishing pad 10 mounted on the table 104, thereby forming micro-holes having a pattern corresponding to the pattern inputted to the CNC controller 102.

That is, the laser device 100 forms, on the polishing pad 10, micro-holes having a shape, size and space respectively corresponding to those inputted to the CNC controller 102, under the control of the CNC controller 102. The shape of each micro-hole such as a circular shape, an oval shape, a triangular shape, or a rectangular or square shape can be determined by adjusting the shape of a laser spot focused onto the polishing pad 10. Also, the diameter or width of each micro-hole to be formed on the polishing pad 10 can be controlled by adjusting the size of the laser spot. For example, when the size of the laser spot is adjusted to be 10 to 150 Em, micro-holes having a diameter of 10 to 150 Em can be formed. Also, where the size of the laser spot is adjusted to be 1 to 100 Em, micro-holes having a diameter of 1 to 100 Em can be formed. The length of each micro-hole and the space between micro-holes arranged adjacent to each other in the travel direction of the laser beam can also be adjusted by controlling the continuous/intermittent irradiation period of the laser beam. The depth of each micro-hole can be adjusted by controlling the power of the laser beam.

Meanwhile, the table 104, on which the polishing pad 10 is mounted, can be moved in three dimensional directions, that is, X, Y, and Z-axis directions, while rotating about an R axis. A desired pattern of micro-holes is formed by the laser beam irradiated onto the polishing pad 10, in accordance with the three-dimensional movements of the table 104 along the X, Y, and Z axes and the rotation of the table 104 under the control of the CNC controller 102 based on the inputted micro-hole pattern. The micro-holes may have a desired angle with respect to the polishing surface. The density and arrangement of the micro-holes may also be adjusted by controlling the moving and rotating speeds of the table 104.

Thus, micro-holes having a desired pattern selected from diverse patterns can be formed on the polishing pad in accordance with a combination of the control for the laser device 100 and the control for the table 104. The formation of grooves or perforations is achieved using the same method as that used in the formation of the micro-holes. Such micro-holes, grooves, and perforations may be selectively formed on the polishing pad 10. Alternatively, they may be formed in the form of a combined pattern. In the latter case, the micro-holes, grooves, and perforations may be sequentially or simultaneously formed.

Figure 9A:
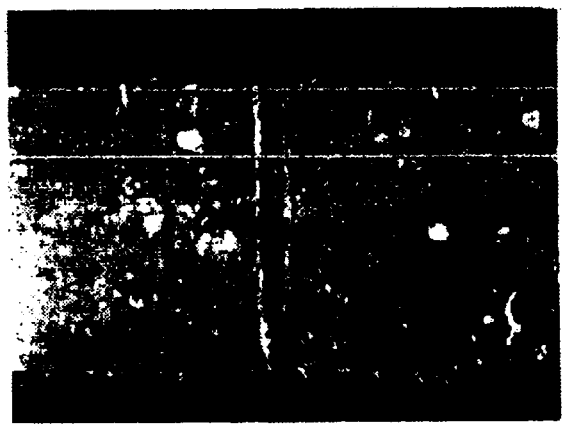
FIG. 9a is a photograph showing the cross-sectional structure of micro-holes formed by a laser in accordance with an embodiment of the present invention.
Figure 9B:
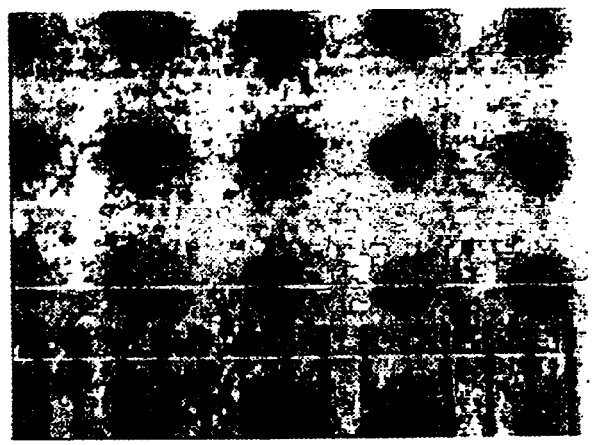
FIG. 9b is a photograph showing the plan structure of the micro-holes formed by the laser in accordance with the embodiment of the present invention.

FIGS. 9a and 9b show photographs of micro-holes formed in accordance with the present invention, respectively.

As shown in FIGS. 9a and 9b, the micro-holes formed in accordance with the present invention have a uniform diameter and a uniform distribution while having a smooth surface. However, microcells of FIGS. 3 and 4 formed in accordance with a conventional method using microelements each having a cavity, or a foaming process, have a non-uniform distribution and a non-uniform size. For this reason, the microcells, which are exposed as the polishing process proceeds, have non-uniform cross sections. The micro-holes of the present invention have the same function as the conventional microcells in that they supply abrasive particles while collecting debris produced during the polishing process, and discharge the collected debris when the polishing pad is reconditioned. In addition, the micro-holes of the present invention have a uniform distribution and a uniform size. Accordingly, the micro-holes of the present invention have considerably superior effects over those of the conventional microcells. In accordance with the present invention, the distribution, density, and size of micro-holes can be freely determined, if desired.

Figure 1:
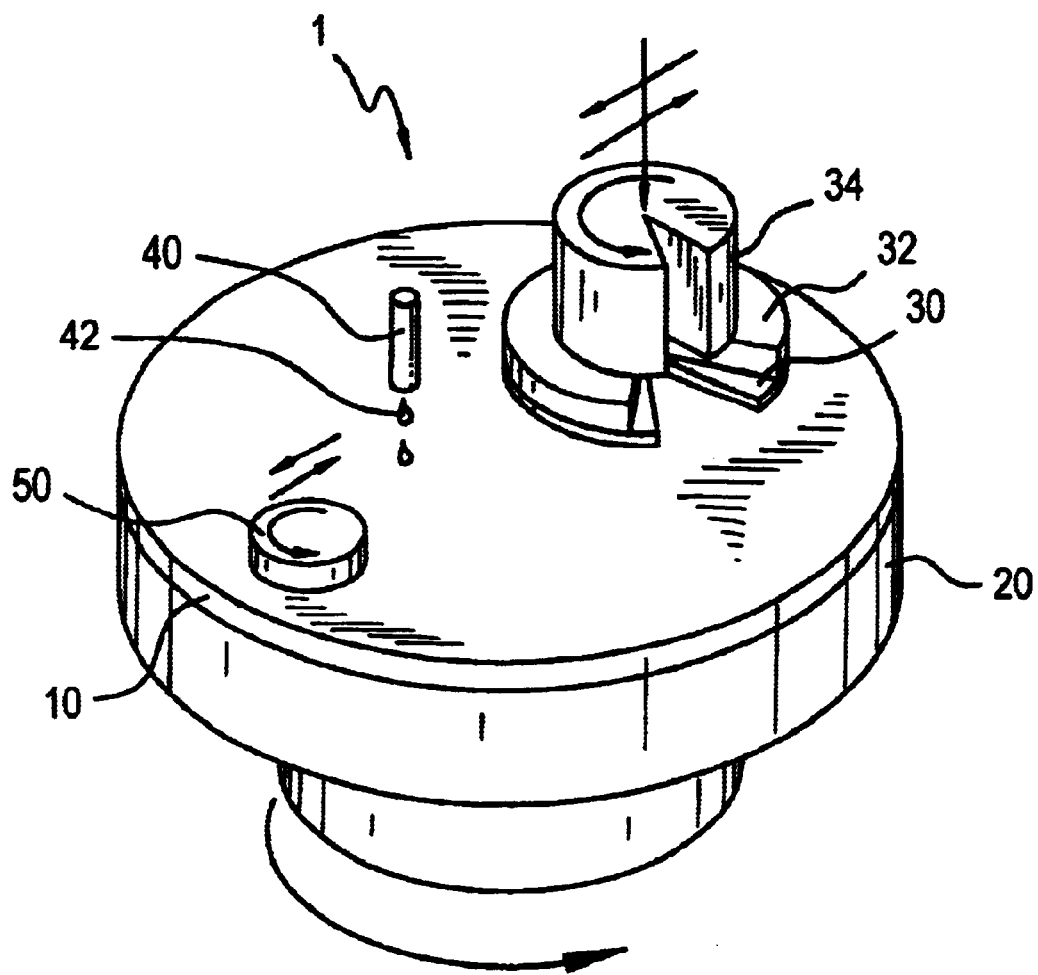
FIG. 1 is a schematic view illustrating the configuration of a typical CMP machine and a polishing method performed using the CMP machine.
Figure 2:
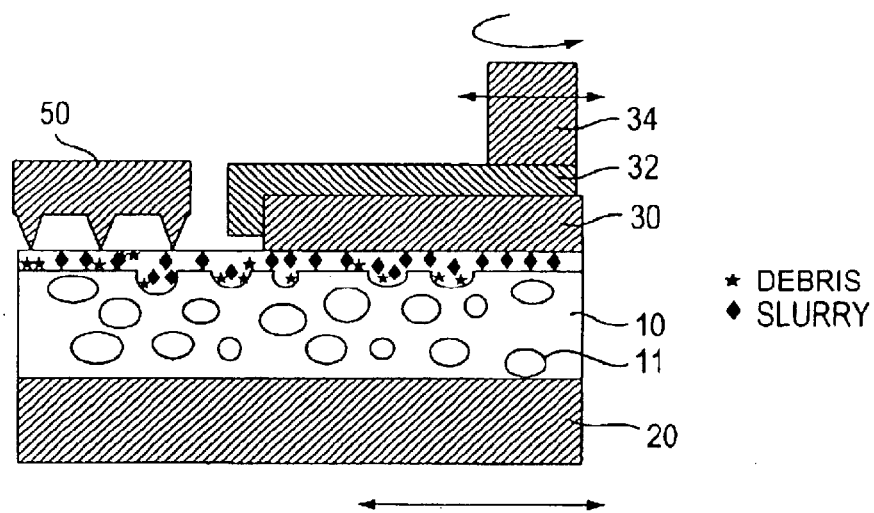
FIG. 2 is a schematic view illustrating the concept of a CMP method.
Figure 3:
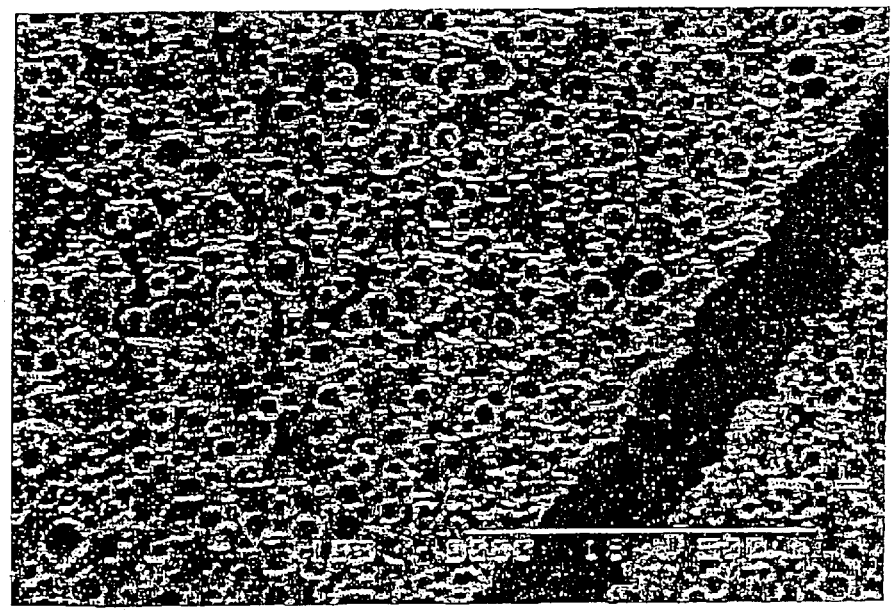
FIG. 3 is a photograph of microcells formed using microelements each having a cavity.
Figure 4:
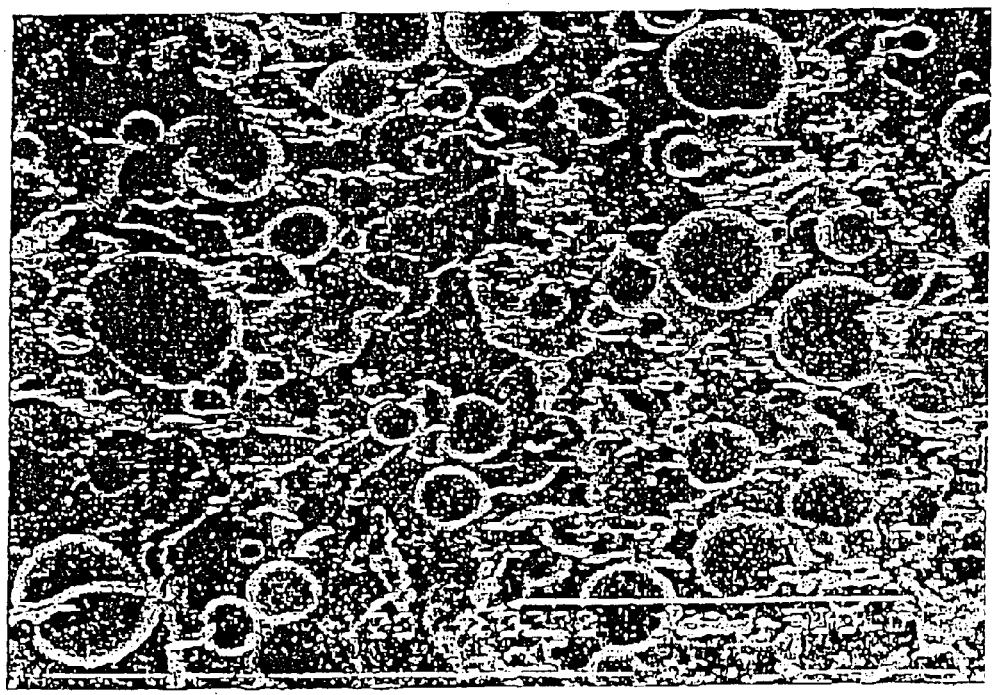
FIG. 4 is a photograph of microcells formed using a foaming method.

The oblique region at the lower right portion of the photograph shown in FIG. 3 represents a perforation formed on a polishing pad using a conventional perforating pin. As shown in FIG. 3, the perforation has a rough surface causing debris to remain in the perforation. Such debris may form scratches on a surface being polished during the CMP process. However, such a problem does not arise with the perforation or groove formed in accordance with the present invention because the perforation or groove has a smooth surface by virtue of a laser machining process. In accordance with the present invention, perforations or grooves having diverse patterns may be freely formed, if desired.

Figure 10:
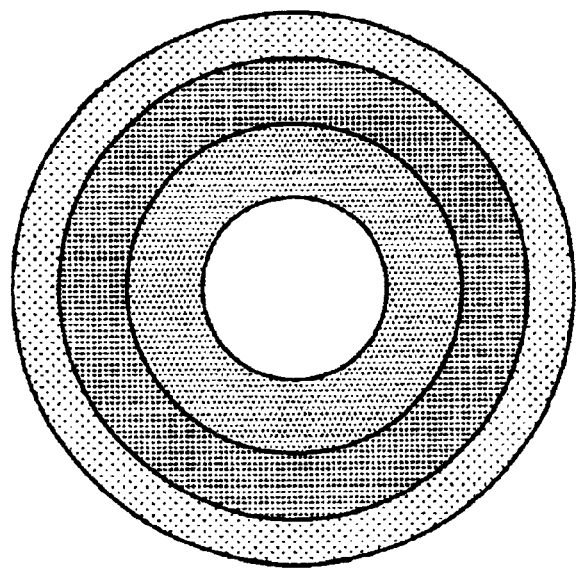
FIG. 10 is a schematic view illustrating a polishing pad having micro-holes formed by the laser in accordance with an embodiment of the present invention.
Figure 11:
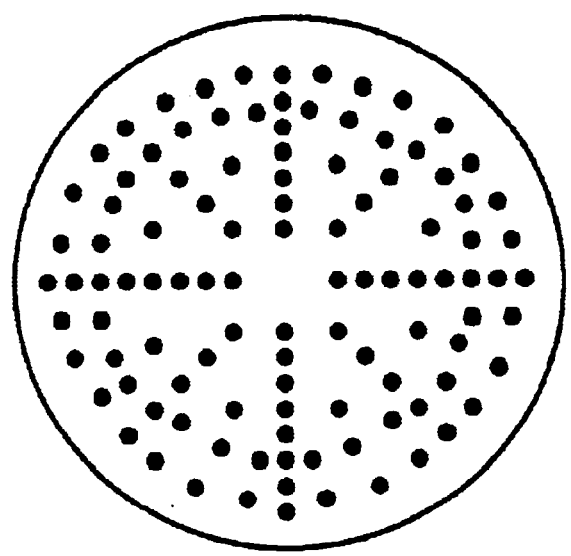
FIG. 11 is a schematic view illustrating a polishing pad having perforations formed by the laser in accordance with another embodiment of the present invention.
Figure 12:
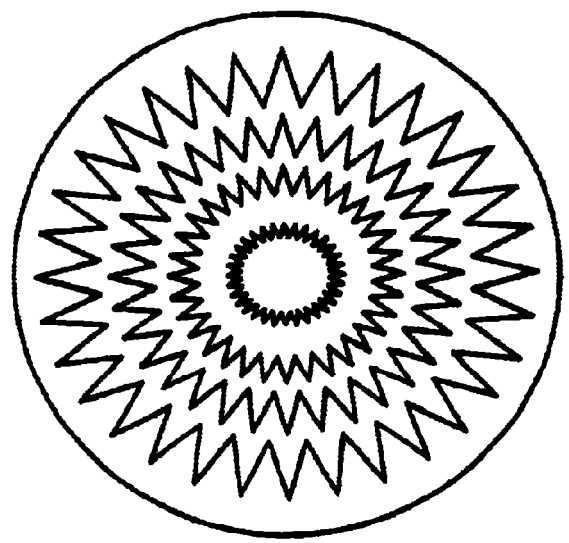
FIG. 12 is a schematic view illustrating a polishing pad having grooves formed by the laser in accordance with another embodiment of the present invention.

FIGS. 10, 11, and 12 are schematic views respectively illustrating embodiments of micro-holes, perforations, and grooves formed in accordance with the present invention.

FIG. 10 is a schematic view illustrating a polishing pad on which micro-holes formed in accordance with the present invention are arranged. The polishing pad shown in FIG. 10 has micro-holes having different densities at different radial regions. In each radial region, the micro-holes have a uniform density and a uniform size.

Figure 5A:
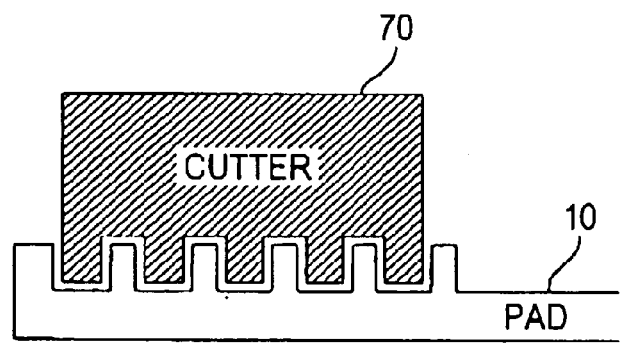
FIG. 5a is schematic view illustrating a conventional cutter for forming grooves.
Figure 5B:
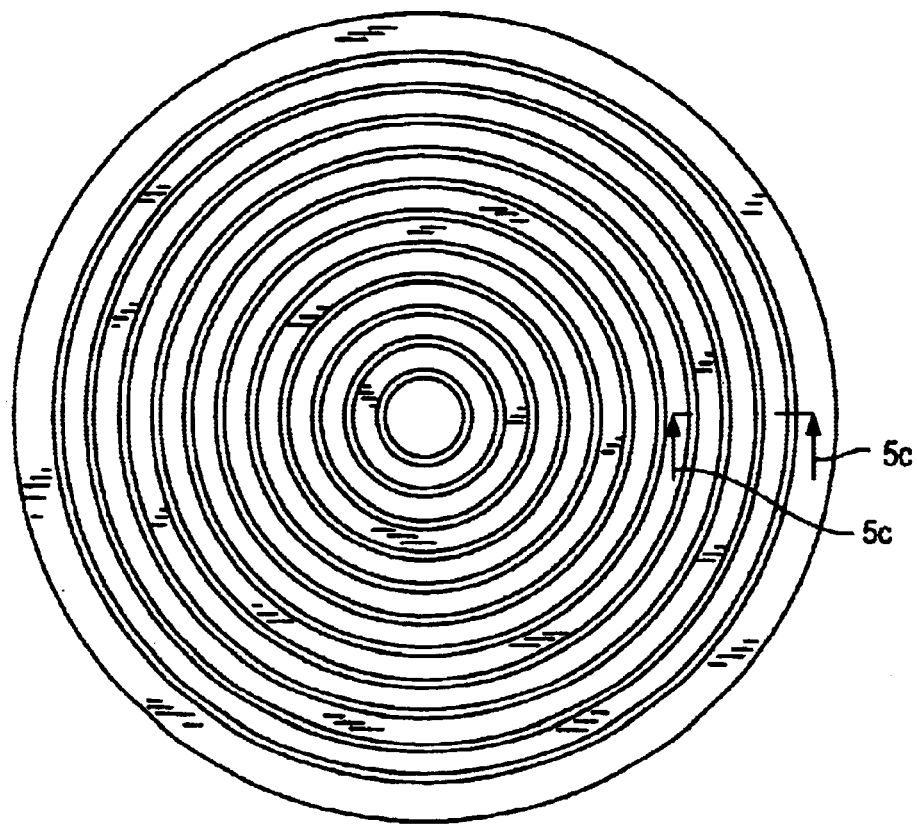
FIG. 5b is a schematic view illustrating a polishing pad having grooves formed in the form of concentric circles using the conventional cutter.
Figure 5C:
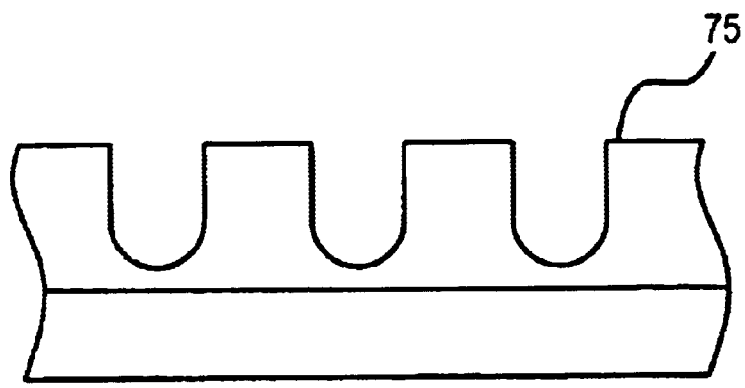
FIG. 5c is a cross-sectional view taken along the line A—A of FIG. 6b.
Figure 6A:
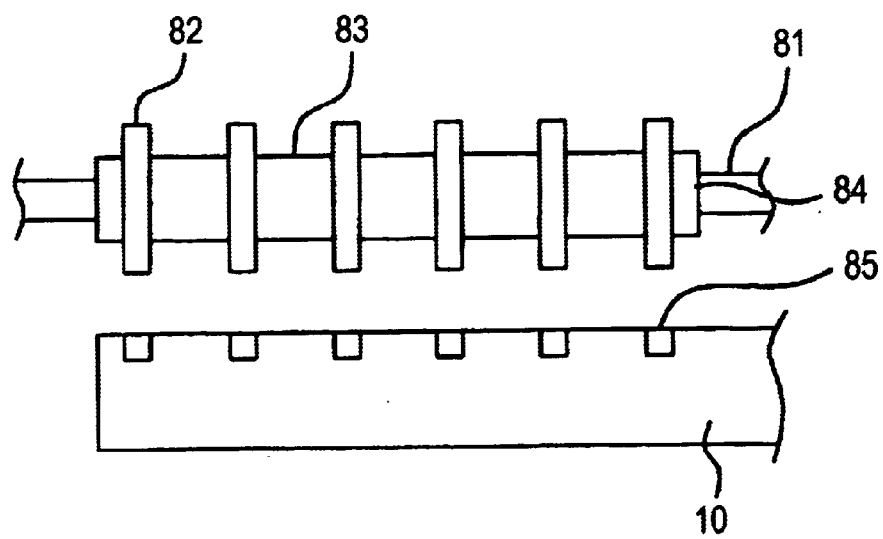
FIG. 6a is a schematic view illustrating a process for forming grooves having a lattice pattern by a conventional horizontal milling machine mounted with conventional cutting saws and spacers.
Figure 6B:
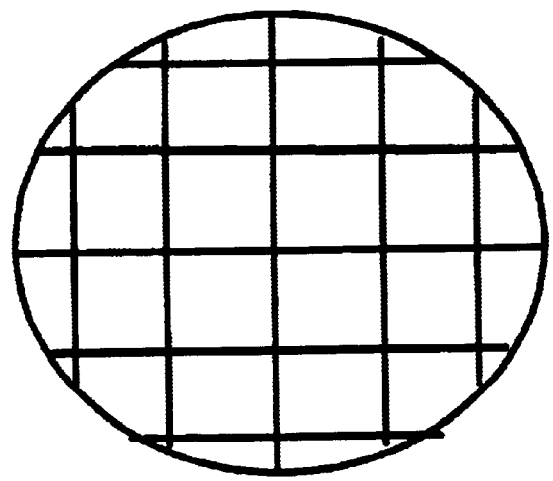
FIG. 6b is a schematic view illustrating a polishing pad having grooves formed in the form of a lattice by the conventional horizontal milling machine.
Figure 6C:
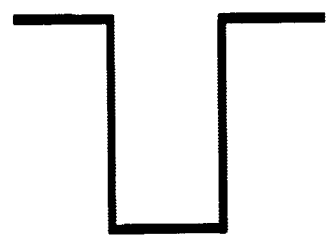
FIG. 6c is a sectional view illustrating one of the lattice-shaped grooves formed by the conventional horizontal milling machine.
Figure 7A:
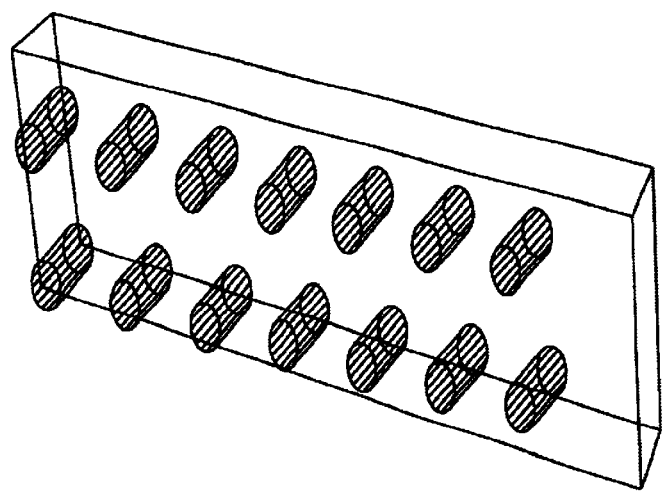
FIG. 7a is a perspective view illustrating perforating pins adapted to form perforations on a polishing pad.
Figure 7B:
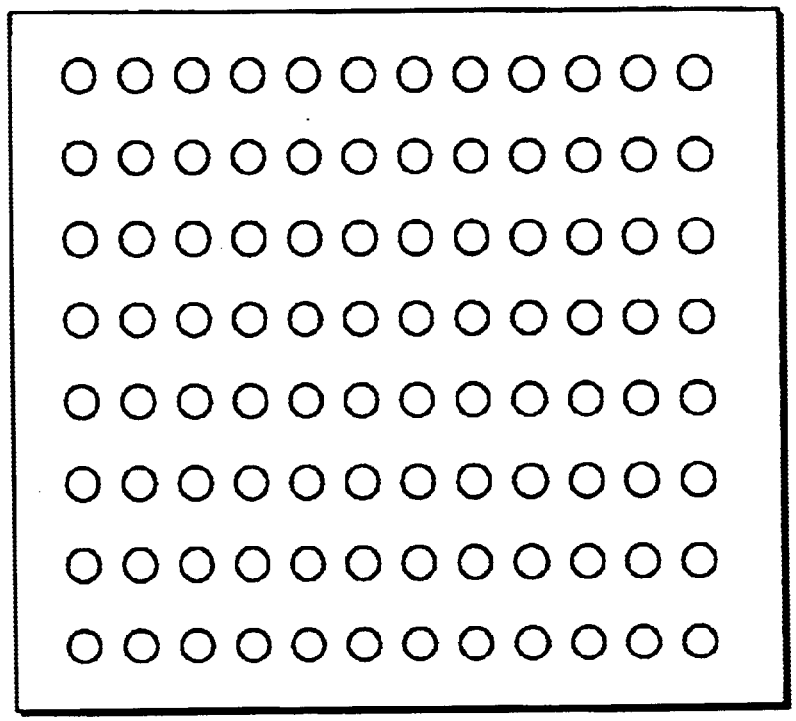
FIG. 7b is a plan view illustrating a process for forming perforations by the convention perforating pins.
Figure 7C:
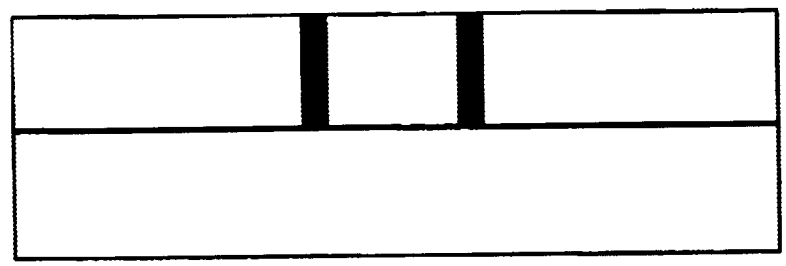
FIG. 7c is a sectional view illustrating a perforating pad having perforations formed by the conventional perforating pins.

FIG. 11 is a schematic view illustrating a polishing pad on which perforations formed in accordance with the present invention are arranged. FIG. 12 is a schematic view illustrating a polishing pad on which grooves formed in accordance with the present invention are arranged. In the case illustrated in FIG. 11 or 12, the machining process is conducted by moving the table in X and Y-axis directions while rotating the table. Although only a fixed pattern of grooves or perforations is formed in accordance with the conventional mechanical machining method, as shown in FIG. 5b, 6b or 7b, unfixed, diverse patterns of micro-holes, grooves or perforations can be freely formed using a CNC controller and a laser in accordance with the present invention.

In accordance with the present invention, the polishing pad can have micro-holes, perforations, or grooves having diverse patterns, without being limited to the patterns illustrated in FIGS. 10, 11, and 12. Also, the polishing pad may have a pattern which is a combination of micro-hole, perforation and groove patterns. For example, the polishing pad may have a combined pattern of micro-holes and perforations, micro-holes and grooves, perforations and grooves, or micro-holes, perforations and grooves.

Industrial Applicability

As apparent from the above description, the present invention provides a method capable of easily forming micro-holes, grooves, or perforations having diverse patterns by a laser. In accordance with the present invention, micro-holes having a uniform distribution and a uniform size are formed on a polishing pad by a laser, thereby maximizing the polishing efficiency of the polishing pad, as compared to conventional polishing pads having non-uniform microcells. The present invention also provides effects of an enhancement in machining efficiency and a reduction in manufacturing costs. In accordance with the present invention, perforations and grooves having precise and diverse patterns can be formed. Accordingly, it is possible to effectively control the flow of a slurry on the polishing pad.

In accordance with the present invention, desired patterns of micro-holes, perforations, and grooves having diverse shape, sizes, and depths, and a combination thereof can be precisely and efficiently formed on a polishing pad by a laser in a short time, based on a given polishing condition. Accordingly, it is possible to achieve an enhancement in manufacturing efficiency and a reduction in manufacturing costs.

Although the preferred embodiments of the invention have been disclosed for illustrative purposes in conjunction with a method for fabricating a polishing pad formed with micro-holes, perforations, or grooves by use of a laser machining process, those skilled in the art will appreciate that various modifications, additions and substitutions are possible, without departing from the scope and spirit of the invention as disclosed in the accompanying claims.

What is claimed is:

1. A method for fabricating a chemical mechanical polishing pad comprising the steps of:

determining a pattern of micro-holes, grooves, or perforated holes to be formed on a polishing pad;

inputting the determined pattern to a computer numerical control (CNC) controller; and driving a laser device adapted to irradiate a laser beam and a table adapted to conduct a three-dimensional movement and rotation while supporting the polishing pad, under a control of the CNC controller based on the inputted pattern, thereby irradiating the laser beam from the laser device onto the polishing pad supported by the table while moving the table in accordance with the inputted pattern, so that micro-holes, grooves, or perforated holes having a pattern corresponding to the determined pattern are formed on the polishing pad.

2. The method according to claim 1, wherein a laser beam spot is adjusted in size to adjust the diameter or width of the micro-holes, grooves or perforations being formed on the polishing pad.

3. The method according to claim 1, wherein continuous and intermittent irradiation periods of the laser beam are controlled to adjust the length of the micro-holes, grooves, or perforations being formed on the polishing pad and the space between the micro-holes, grooves, or perforations arranged adjacent to each other in a travel direction of the laser beam.

4. The method according to claim 1, wherein the laser beam is controlled in power to adjust the depth of the micro-holes, grooves, or perforations being formed on the polishing pad.

5. The method according to claim 1, wherein the table is moved in X, Y, and Z-axis directions to adjust an angle defined by the micro-holes, grooves, or perforations being formed on the polishing pad with respect to a polishing surface of the polishing pad.

* * * * *